United States Patent
McIntyre

(10) Patent No.: US 9,089,141 B2
(45) Date of Patent: Jul. 28, 2015

(54) NATURAL INSECT REPELLENT FORMULA BBX2

(71) Applicant: John James McIntyre, Shingle Springs, CA (US)

(72) Inventor: John James McIntyre, Shingle Springs, CA (US)

( * ) Notice: Subject to any disclaimer, the term of this patent is extended or adjusted under 35 U.S.C. 154(b) by 61 days.

(21) Appl. No.: 13/987,968

(22) Filed: Sep. 20, 2013

(65) Prior Publication Data

US 2015/0086652 A1    Mar. 26, 2015

(51) Int. Cl.
| | | |
|---|---|---|
| A61K 36/185 | (2006.01) | |
| A61K 36/47 | (2006.01) | |
| A01N 65/06 | (2009.01) | |
| A01N 37/06 | (2006.01) | |
| A01N 25/04 | (2006.01) | |
| A01N 25/08 | (2006.01) | |
| A01N 65/12 | (2009.01) | |

(52) U.S. Cl.
CPC .............. *A01N 65/06* (2013.01); *A01N 25/04* (2013.01); *A01N 25/08* (2013.01); *A01N 37/06* (2013.01); *A01N 65/12* (2013.01)

(58) Field of Classification Search
None
See application file for complete search history.

(56) References Cited

U.S. PATENT DOCUMENTS

| | | | | |
|---|---|---|---|---|
| 5,621,013 | A * | 4/1997 | Beldock et al. | 514/703 |
| 5,885,600 | A * | 3/1999 | Blum et al. | 424/405 |
| 8,206,763 | B2 * | 6/2012 | Porter et al. | 424/739 |
| 8,252,299 | B1 * | 8/2012 | Kiernan, Jr. | 424/405 |
| 2006/0223878 | A1 * | 10/2006 | Scialdone | 514/427 |
| 2009/0233940 | A1 * | 9/2009 | Taylor | 514/252.12 |
| 2009/0257959 | A1 * | 10/2009 | Sims | 424/45 |
| 2010/0247684 | A1 * | 9/2010 | Reid et al. | 424/725 |
| 2013/0156839 | A1 * | 6/2013 | Messina et al. | 424/410 |
| 2013/0295153 | A1 * | 11/2013 | Miresmailli et al. | 424/409 |

* cited by examiner

*Primary Examiner* — Chris R Tate

(57) ABSTRACT

The natural insect repellent BBX2 is a composition of refined oils such as Citronella, Cedar, Mineral, Castor, and Oleic Acid with Diatomaceous Earth to repel insects from landing on and remaining on human skin. It can be made in many different forms such as liquid, lotion, spray, paste, cream and can be a part of articles such as animal collars, garbage bags, planting material, and of course fabrics for clothing, tents, and anything that a person would use or wear.

1 Claim, No Drawings

NATURAL INSECT REPELLENT FORMULA BBX2

BACKGROUND OF THE INVENTION (1) Field of the Invention

The Natural Insect Repellent is new formula using all natural ingredients in percentages that are unique and are in compliance with an all-natural product FDA category list.

(2) Description of the Art Including Information Disclosed under 37 CFR 1.97 & 1.98

The art described in this utility specification and in this application is unique however there numerous existing patents that we have cited as similar in nature. Many patents such as U.S. Pat. Nos. 8,206,763—8,252,299—5,885,600—5,621,013—and others that use natural oils such as Citronella, Cedar Wood, Mineral, and White Mineral in different percentages and in different combinations. As seen in this specification this formula adds numerous oils and diatomaceous earth in unique percentages that have been used in real life situations.

BRIEF SUMMARY OF THE INVENTION

The natural insect repellent formula BBX2 is a combination of oils that are made from cold compression and refined as with any oil that is used for consumer or commercial use and which have extended shelf life and have been proven to repel insects of many types. In addition an oleic acid with diatomaceous earth has been added as an additional deterrent for insects making contact with human skin in combination with the oils to make this formula highly effective for an insect repellent.

DETAILED DESCRIPTION OF THE INVENTION

The majority of refined oils sold commercially are either processed solvents, filtered, steam distilled or a combination. These oils such as Citronella, Mineral, White Mineral, Cedar Wood, have been proven over the years of use to be effective in using them as insect repellents and have been used in other patents and products on the market today. They are part of the public domain however in combination used with other additives in certain percentages and with addition of the Diatomaceous Earth, Oleic Acid, and Castor Oil the formula within this specification is unique and has proven to work very effectively in the real world.

Being the owner of a termite and pest control company the inventor has used this formula in a real life environment and has added Diatomaceous Earth to the original formula. Diatomaceous Earth particles on a microscopic level are very sharp looking because they are made of pure silica which is what glass is made of. These particles stick to an insect and get stuck between its exoskeleton joints. As the insect moves, it gets physically cut up. The other explanation is that diatomaceous earth sticks to the insect which involves scratching the insects waxy layer which then allows precious moisture within the insect to dry out. It also acts as a deterrent to insects because of its natural make up to act as tiny razor blades that the insect would walk upon or make contact with. It irritates the insect very quickly and to such a degree that the insect flies away once it lands on human skin if it is not affected by the odor of the oils. It can also act as a warning to other insects.

In addition an Oleic Acid is used to help the properties absorb into the skin lasting longer. Oleic acid's high lipid count makes it a great moisturizer, and a number of cosmetic companies add it to lotions and soaps in order to boost their ability to nourish the skin. The acid is often able to penetrate past the outer skin layer, which leads to a much longer-lasting and more intense moisture. While standard lotions and creams may simply sit on the top of the skin, those made with omega-9 fatty acids typically go much deeper, producing more satisfying results and often commanding a higher price.

In addition scientists who study bee and ant colonies have discovered that oleic acid may also play a key role in warning colony members of death or coming danger. Most bee and ant species secrete the acid as a pheromone, which is a type of hormone that is detected by smell. When they die, their corpses tend to emit high levels of this pheromone, possibly as a warning to others. If the insect died because of something it ate or some other danger in the area, the acid's smell will serve as a warning to others to stay away. It may also be a signal for colony members to come and collect the corpse, a common practice in species that perform group rituals for fallen members.

The key in this formula is to use a certain percentage of oils with the Diatomaceous Earth and the Oleic Acid to total 100%. With this formula you have the Mineral Oil at 88.4%, Castor Oil at 5.8%, Citronella Oil at 0.6%, Cedar Oil at 0.8%, Oleic Acid at 3.4%, and Diatomaceous Earth at 0.9% which complies with the FDA for 100% natural products sold to the public.

This formula is totally non-toxic and is very effective with a neutral aroma to humans which could be enhanced with other scents in the future. It can be applied by spray, lotion, liquid, paste, and can be interfused with fabrics for clothing, tents, bed clothing, garbage bags, planting materials, and can be applied to surfaces other than human skin. It can also be used on animals which is an inexpensive way to prevent diseases and infection in livestock and house pets.

What is claimed is:

1. An insect repellent formulation consisting essentially of:
   (a) mineral oil, in an amount of 88.4%;
   (b) castor oil, in an amount of 5.8%;
   (c) citronella oil, in an amount of 0.6%;
   (d) cedar oil, in an amount of 0.8%;
   (e) oleic acid, in an amount of 3.4%; and
   (f) diatomaceous earth, in an amount of 0.9%.

* * * * *